(12) United States Patent
McGuckin, Jr. et al.

(10) Patent No.: US 11,253,292 B2
(45) Date of Patent: Feb. 22, 2022

(54) ATHERECTOMY DEVICE

(71) Applicant: Rex Medical, L.P., Conshohocken, PA (US)

(72) Inventors: James F. McGuckin, Jr., Radnor, PA (US); John D. Leedle, Chicago, IL (US); Colin Valentis, Lansdale, PA (US); Jenna Rose Israel, Philadelphia, PA (US)

(73) Assignee: Rex Medical, L.P., Conshohocken, PA (US)

( * ) Notice: Subject to any disclaimer, the term of this patent is extended or adjusted under 35 U.S.C. 154(b) by 750 days.

(21) Appl. No.: 15/242,557

(22) Filed: Aug. 21, 2016

(65) Prior Publication Data
US 2017/0071624 A1    Mar. 16, 2017

Related U.S. Application Data

(60) Provisional application No. 62/217,963, filed on Sep. 13, 2015.

(51) Int. Cl.
*A61B 17/3207* (2006.01)
*A61M 1/00* (2006.01)
*A61B 17/3203* (2006.01)

(52) U.S. Cl.
CPC .. *A61B 17/320783* (2013.01); *A61B 17/3203* (2013.01); *A61B 17/3207* (2013.01);
(Continued)

(58) Field of Classification Search
CPC ........ A61B 17/320783; A61B 17/3207; A61B 17/320708; A61B 17/32075;
(Continued)

(56) References Cited

U.S. PATENT DOCUMENTS 4,445,509 A * 5/1984 Auth .............. A61B 17/320758
606/159
4,883,458 A    11/1989 Shiber
(Continued)

FOREIGN PATENT DOCUMENTS

CN    102670283    9/2012
EP    2 913 012    9/2015
(Continued)

OTHER PUBLICATIONS

The Extended European Search Report Application No. 16187574.5 dated Jan. 30, 2017.
(Continued)

*Primary Examiner* — Richard G Louis
(74) *Attorney, Agent, or Firm* — Neil D. Gershon

(57) ABSTRACT

A surgical atherectomy apparatus for removing particles such as plaque from an interior of a vessel having a motor housing slidable axially between a proximal position and a distal position. An axially fixed sheath extends from the outer housing and a catheter is connected to the motor housing and is positioned within the sheath. A rotatable shaft is positioned within the lumen of the catheter and is operatively connected to the motor for rotational movement, the rotatable shaft and catheter movable by movement of the motor housing between the proximal and distal positions. The rotatable shaft has an atherectomy bit extending therefrom for dislodgement of particles when rotated by the motor and dislodged particles are aspirated in the lumen of the catheter.

6 Claims, 5 Drawing Sheets

(52) U.S. Cl.
CPC ............... *A61B 17/32075* (2013.01); *A61B 17/320758* (2013.01); *A61M 1/0058* (2013.01); *A61B 2017/320766* (2013.01)

(58) Field of Classification Search
CPC ........ A61B 17/3203; A61B 17/320758; A61B 2017/320733; A61B 2017/320741; A61B 2017/320766; A61B 2017/320775; A61M 1/0058

See application file for complete search history.

(56) References Cited

U.S. PATENT DOCUMENTS

| | | | |
|---|---|---|---|
| 4,957,482 A | 9/1990 | Shiber | |
| 4,979,939 A | 12/1990 | Shiber | |
| 4,990,134 A | 2/1991 | Auth | |
| 5,019,089 A | 5/1991 | Farr | |
| 5,047,040 A | 9/1991 | Simpson | |
| 5,114,399 A | 5/1992 | Kovalcheck | |
| 5,217,474 A | 6/1993 | Zacca et al. | |
| 5,273,526 A | 12/1993 | Dance | |
| 5,287,858 A | 2/1994 | Hammerslag | |
| 5,306,244 A | 4/1994 | Shiber | |
| 5,308,354 A | 5/1994 | Zacca | |
| 5,312,427 A * | 5/1994 | Shturman | A61B 17/3207 606/159 |
| 5,314,438 A * | 5/1994 | Shturman | A61B 17/320758 606/159 |
| 5,356,418 A * | 10/1994 | Shturman | A61B 17/320758 606/159 |
| 5,490,859 A | 2/1996 | Mische | |
| 5,584,843 A | 12/1996 | Wulfman | |
| 5,632,755 A | 5/1997 | Nordgren et al. | |
| 5,653,696 A | 8/1997 | Shiber | |
| 5,667,490 A | 9/1997 | Keith | |
| 5,681,336 A | 10/1997 | Clement et al. | |
| 5,728,129 A * | 3/1998 | Summers | A61B 17/320758 606/159 |
| 5,779,721 A | 7/1998 | Nash | |
| 5,794,626 A | 8/1998 | Kieturakis | |
| 5,873,882 A | 2/1999 | Straub et al. | |
| 5,876,414 A | 3/1999 | Straub | |
| 5,879,361 A | 3/1999 | Nash | |
| 5,938,670 A | 8/1999 | Keith et al. | |
| 5,938,672 A | 8/1999 | Nash | |
| 5,951,581 A | 9/1999 | Saadat | |
| 5,976,165 A | 11/1999 | Ball et al. | |
| 6,001,112 A | 12/1999 | Taylor | |
| 6,015,420 A | 1/2000 | Wulfman et al. | |
| 6,066,152 A | 5/2000 | Strauss et al. | |
| 6,077,282 A | 6/2000 | Shturman et al. | |
| 6,080,170 A | 6/2000 | Nash et al. | |
| 6,090,118 A | 7/2000 | McGuckin, Jr. | |
| 6,113,615 A | 9/2000 | Wulfman | |
| 6,132,444 A | 10/2000 | Shturman | |
| 6,146,395 A | 11/2000 | Kanz et al. | |
| 6,156,046 A | 12/2000 | Passafaro et al. | |
| 6,156,048 A | 12/2000 | Wulfman et al. | |
| 6,183,487 B1 | 2/2001 | Barry et al. | |
| 6,206,898 B1 | 3/2001 | Honeycutt et al. | |
| 6,270,509 B1 | 8/2001 | Barry et al. | |
| 6,299,623 B1 | 10/2001 | Wulfman | |
| 6,443,967 B1 | 9/2002 | Kadavy et al. | |
| 6,454,779 B1 | 9/2002 | Taylor | |
| 6,482,216 B1 | 11/2002 | Hiblar et al. | |
| 6,491,660 B2 | 12/2002 | Guo et al. | |
| 6,494,890 B1 | 12/2002 | Shturman et al. | |
| 6,497,711 B1 | 12/2002 | Plaia et al. | |
| 6,565,588 B1 | 5/2003 | Clement | |
| 6,569,147 B1 | 5/2003 | Evans et al. | |
| 6,569,177 B1 | 5/2003 | Dillard et al. | |
| 6,572,630 B1 | 6/2003 | McGuckin, Jr | |
| 6,579,298 B1 * | 6/2003 | Bruneau | A61B 17/320758 606/159 |
| 6,579,299 B2 | 6/2003 | McGuckin, Jr. et al. | |
| 6,596,005 B1 | 7/2003 | Kanz et al. | |
| 6,602,264 B1 | 8/2003 | McGuckin, Jr. | |
| 6,626,890 B2 | 9/2003 | Nguyen et al. | |
| 6,632,230 B2 | 10/2003 | Barry | |
| 6,652,546 B1 | 11/2003 | Nash et al. | |
| 6,702,830 B1 | 3/2004 | Demarais et al. | |
| 6,752,630 B2 | 6/2004 | Roetzer | |
| 6,808,531 B2 | 10/2004 | Lafontaine et al. | |
| 6,824,550 B1 | 11/2004 | Noriega et al. | |
| 6,830,577 B2 | 12/2004 | Nash et al. | |
| 6,843,797 B2 | 1/2005 | Nash et al. | |
| 6,905,505 B2 | 6/2005 | Nash et al. | |
| 6,926,725 B2 | 8/2005 | Cooke et al. | |
| 6,936,056 B2 | 8/2005 | Nash et al. | |
| 7,037,316 B2 | 5/2006 | McGuckin, Jr. et al. | |
| 7,172,610 B2 | 2/2007 | Heitzmann et al. | |
| 7,479,147 B2 | 1/2009 | Honeycutt et al. | |
| 7,534,249 B2 | 5/2009 | Nash et al. | |
| 7,645,261 B2 | 1/2010 | Hinchliffe | |
| 7,655,016 B2 | 2/2010 | Demarais | |
| 7,666,161 B2 | 2/2010 | Nash et al. | |
| 7,713,231 B2 | 5/2010 | Wulfman et al. | |
| 7,771,445 B2 | 8/2010 | Heitzmann et al. | |
| 7,833,239 B2 | 11/2010 | Nash | |
| 7,905,896 B2 | 3/2011 | Straub | |
| 7,959,608 B2 | 6/2011 | Nash et al. | |
| 7,976,528 B2 | 7/2011 | Nash et al. | |
| 7,981,128 B2 | 7/2011 | To et al. | |
| 7,981,129 B2 | 7/2011 | Nash et al. | |
| 8,007,506 B2 | 8/2011 | To et al. | |
| 8,062,317 B2 | 11/2011 | McGuckin, Jr. et al. | |
| 8,109,954 B2 | 2/2012 | Shturman | |
| 8,142,458 B2 | 3/2012 | Shturman | |
| 8,226,673 B2 | 7/2012 | Nash et al. | |
| 8,236,016 B2 | 8/2012 | To et al. | |
| 8,323,240 B2 | 12/2012 | Wulfman et al. | |
| 8,348,965 B2 | 1/2013 | Prudnikov et al. | |
| 8,353,922 B2 | 1/2013 | Noriega | |
| 8,353,923 B2 | 1/2013 | Shturman | |
| 8,361,094 B2 | 1/2013 | To et al. | |
| 8,361,097 B2 | 1/2013 | Patel et al. | |
| 8,388,582 B2 | 3/2013 | Eubanks et al. | |
| 8,414,543 B2 | 4/2013 | McGuckin, Jr. et al. | |
| 8,439,937 B2 | 5/2013 | Montague et al. | |
| 8,465,511 B2 | 6/2013 | McGuckin, Jr. et al. | |
| 8,475,484 B2 | 7/2013 | Wulfman et al. | |
| 8,551,128 B2 | 10/2013 | Hanson et al. | |
| 8,568,432 B2 | 10/2013 | Straub | |
| 8,574,249 B2 | 11/2013 | Moberg | |
| 8,579,851 B2 | 11/2013 | Cull | |
| 8,597,313 B2 | 12/2013 | Thatcher et al. | |
| 8,628,549 B2 | 1/2014 | To et al. | |
| 8,628,550 B2 | 1/2014 | Narveson et al. | |
| 8,628,551 B2 | 1/2014 | Hanson et al. | |
| 8,632,557 B2 | 1/2014 | Thatcher et al. | |
| 8,663,259 B2 | 3/2014 | Levine et al. | |
| 8,663,261 B2 | 3/2014 | Shturman | |
| 8,702,735 B2 | 4/2014 | Rivers | |
| 8,758,377 B2 | 6/2014 | Rivers et al. | |
| 8,764,779 B2 | 7/2014 | Levine et al. | |
| 8,795,303 B2 | 8/2014 | McBroom et al. | |
| 8,795,304 B2 | 8/2014 | Svendsen et al. | |
| 8,795,306 B2 | 8/2014 | Smith et al. | |
| 8,882,680 B2 | 11/2014 | Furlong et al. | |
| 8,888,801 B2 | 11/2014 | To et al. | |
| 8,920,402 B2 | 12/2014 | Nash et al. | |
| 9,023,070 B2 | 5/2015 | Levine et al. | |
| 9,028,424 B2 | 5/2015 | Furlong et al. | |
| 9,033,864 B2 | 5/2015 | Furlong et al. | |
| 9,033,895 B2 | 5/2015 | Furlong et al. | |
| 9,050,126 B2 | 6/2015 | Rivers et al. | |
| 9,055,966 B2 | 6/2015 | Cambronne et al. | |
| 9,072,505 B2 | 7/2015 | Furlong et al. | |
| 9,113,945 B2 | 8/2015 | Malla et al. | |
| 9,119,660 B2 | 9/2015 | Rivers et al. | |
| 9,119,661 B2 | 9/2015 | Rivers et al. | |
| 9,211,138 B2 | 12/2015 | Shturman | |
| 9,675,376 B2 | 6/2017 | To | |

(56) References Cited

U.S. PATENT DOCUMENTS

| | | | |
|---|---|---|---|
| 2002/0007190 A1* | 1/2002 | Wulfman | A61B 17/320725 606/167 |
| 2002/0099367 A1 | 7/2002 | Guo et al. | |
| 2002/0138088 A1 | 9/2002 | Nash | |
| 2003/0125757 A1 | 7/2003 | Patel | |
| 2003/0199889 A1 | 10/2003 | Kanz et al. | |
| 2004/0219028 A1 | 11/2004 | Demarais et al. | |
| 2004/0243162 A1 | 12/2004 | Wulfman et al. | |
| 2005/0080478 A1 | 4/2005 | Barongan | |
| 2005/0119678 A1 | 6/2005 | O'Brien | |
| 2005/0149084 A1 | 7/2005 | Kanz et al. | |
| 2007/0162062 A1* | 7/2007 | Norton | A61B 17/32002 606/170 |
| 2008/0004643 A1 | 1/2008 | To et al. | |
| 2009/0018565 A1* | 1/2009 | To | A61B 17/320758 606/159 |
| 2009/0024085 A1 | 1/2009 | To et al. | |
| 2011/0040315 A1 | 2/2011 | To et al. | |
| 2011/0106051 A1 | 5/2011 | Saab | |
| 2011/0270289 A1 | 11/2011 | To et al. | |
| 2012/0071907 A1 | 3/2012 | Pintor et al. | |
| 2012/0130410 A1 | 5/2012 | Tai et al. | |
| 2012/0211542 A1 | 8/2012 | Racenet | |
| 2013/0018398 A1* | 1/2013 | Rivers | A61B 17/320758 606/159 |
| 2013/0018399 A1 | 1/2013 | Rivers et al. | |
| 2013/0023913 A1 | 1/2013 | Rivers et al. | |
| 2013/0103046 A1 | 4/2013 | Shiber | |
| 2013/0178868 A1 | 7/2013 | Roh | |
| 2013/0245704 A1 | 9/2013 | Koltz et al. | |
| 2013/0253552 A1 | 9/2013 | Schoenle et al. | |
| 2014/0148830 A1 | 5/2014 | Bowman | |
| 2014/0200599 A1 | 7/2014 | Shiber | |
| 2014/0316451 A1 | 10/2014 | Higgins et al. | |
| 2014/0330286 A1 | 11/2014 | Wallace | |
| 2015/0051626 A1 | 2/2015 | Rivers et al. | |
| 2015/0094748 A1 | 4/2015 | Nash et al. | |
| 2015/0164542 A1 | 6/2015 | Wulfman et al. | |
| 2015/0245851 A1 | 9/2015 | McGuckin, Jr. | |
| 2015/0342682 A1 | 12/2015 | Bowe | |

FOREIGN PATENT DOCUMENTS

| | | | |
|---|---|---|---|
| NL | 1034242 | 8/2008 | |
| WO | WO 1994/10919 | 5/1994 | |
| WO | WO1998/004199 | 2/1998 | |
| WO | WO 01/19444 | 3/2001 | |
| WO | WO 2001/076680 | 10/2001 | |
| WO | WO 02/26289 | 4/2002 | |
| WO | WO 2008/097993 | 8/2008 | |
| WO | WO 2008/155759 | 12/2008 | |
| WO | WO 2012/088167 | 6/2012 | |
| WO | WO 2014/91881 | 6/2014 | |
| WO | WO 2014/163942 | 10/2014 | |

OTHER PUBLICATIONS

European Search Report for application 17161776.4-1659 dated Jul. 2017.
The Extended European Search Report Application No. 15155876.4 dated Jul. 6, 2015.
The Extended European Search Report Application No. 15200337.2 dated Apr. 28, 2016.
The Extended European Search Report Application No. 15200337.2 dated Nov. 18, 2020.

* cited by examiner

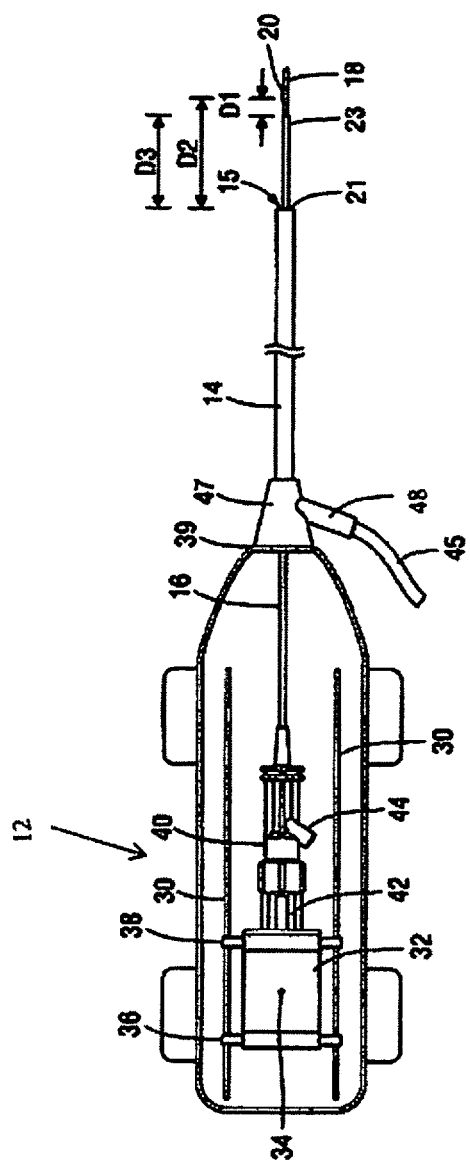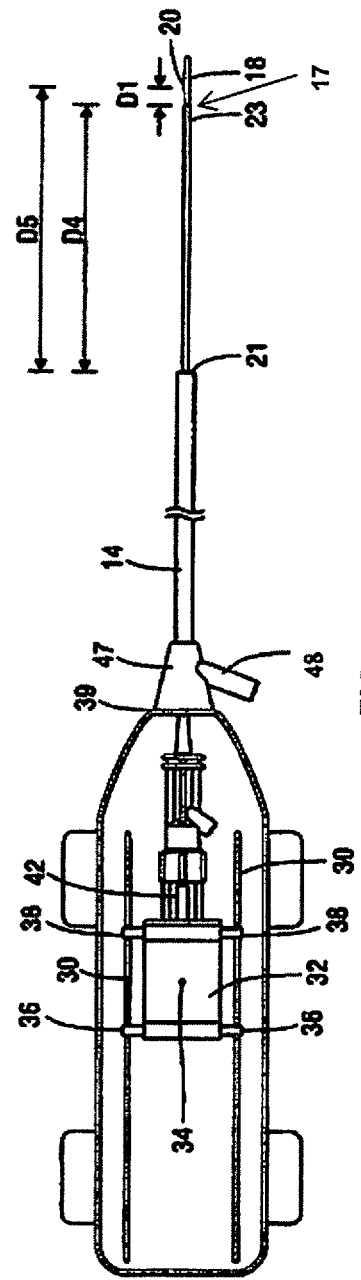

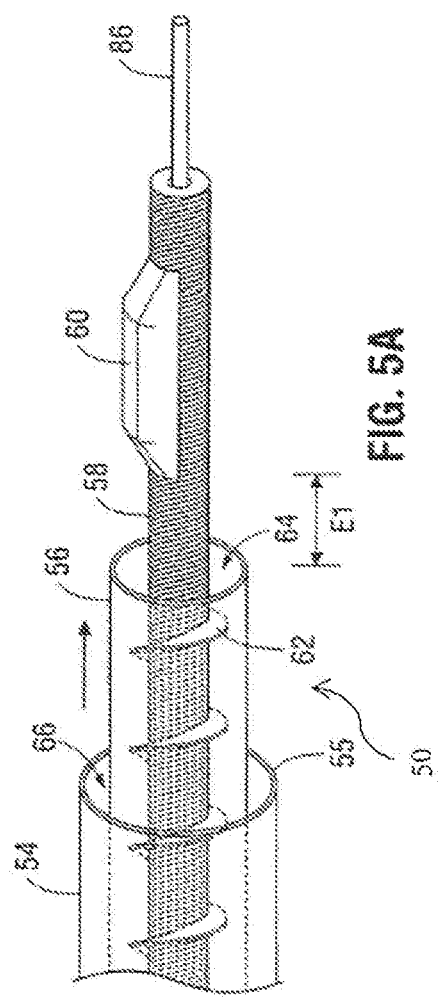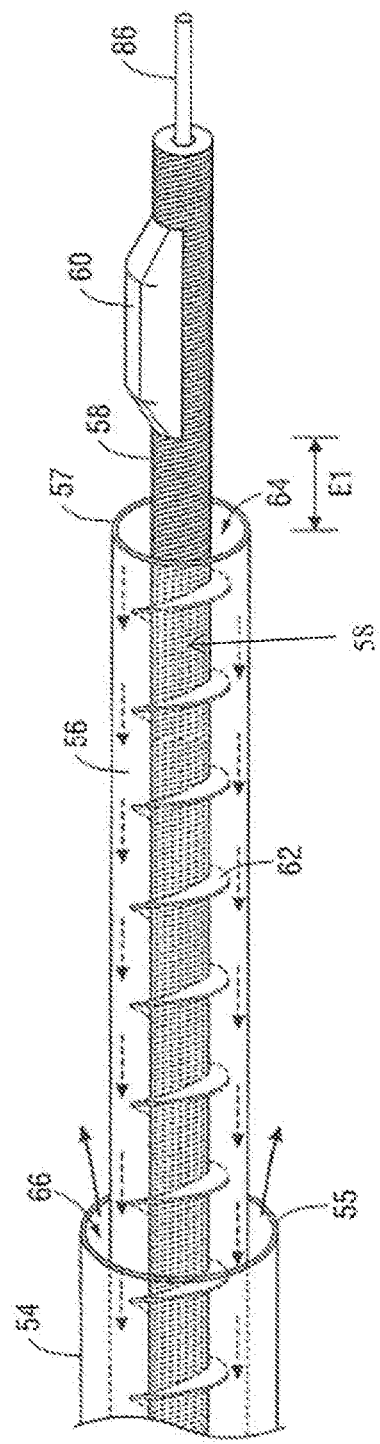

ATHERECTOMY DEVICE

This application claims priority from provisional application Ser. No. 62/217,963, filed Sep. 13, 2015, the entire contents of which are incorporated herein by reference.

BACKGROUND

Technical Field

This application relates to a vascular surgical apparatus, and more particularly to a minimally invasive device for removing plaque or other deposits from the interior of a vessel.

Background of Related Art

The vascular disease of atherosclerosis is the buildup of plaque or substances inside the vessel, e.g., arterial, wall which reduces the size of the passageway through the vessel, thereby restricting blood flow. Such constriction or narrowing of the passage in the vessel is referred to as stenosis. In the case of peripheral vascular disease, which is atherosclerosis of the vascular extremities, if the vessel constriction is left untreated, the resulting insufficient blood flow can cause claudication and possibly require amputation of the patient's limb. In the case of coronary artery disease, if left untreated, the blood flow through the coronary artery to the myocardium will become inadequate causing myocardial infarction and possibly leading to stroke and even death.

There are currently several different treatments for treating arterial disease. The most invasive treatment is major surgery. With peripheral vascular diseases, such as occlusion of the tibial artery, major surgery involves implantation and attachment of a bypass graft to the artery so the blood flow will bypass the occlusion. The surgery involves a large incision, e.g., a 10 inch incision in the leg, is expensive and time consuming for the surgeon, increases patient pain and discomfort, results in a long patient recovery time, and has the increased risk of infection with the synthetic graft.

Major surgery for treating coronary artery disease is even more complex. In this surgery, commonly referred to as open heart surgery, a bypass graft connects the heart to the vessel downstream of the occlusion, thereby bypassing the blockage. Bypass surgery requires opening the patient's chest, is complex, has inherent risks to the patient, is expensive and requires lengthy patient recovery time. Bypass surgery also requires use of a heart lung machine to pump the blood as the heart is stopped, which has its own risks and disadvantages. Oftentimes, the saphenous vein in the patient's leg must be utilized as a bypass graft, requiring the additional invasive leg incision which further complicates the procedure, increases surgery time, lengthens the patient's recovery time, can be painful to the patient, and increases the risk of infection.

Attempts to minimize the invasiveness of coronary bypass surgery are currently being developed and utilized in certain instances. These typically include cracking a few ribs and creating a "window approach" to the heart. Although the window approach may reduce patient trauma and recovery time relative to open heart surgery, it still requires major surgery, and is a complicated and difficult surgery to perform due to limited access and limited instrumentation for successfully performing the operation. Attempts to avoid the use of a heart lung machine by using heart stabilization methods is becoming more accepted, but again, this does not avoid major surgery.

Due to these problems with major peripheral or coronary vascular surgery, minimally invasive procedures have been developed. Balloon angioplasty is one of the minimally invasive methods for treating vessel occlusion/obstructions. Basically, a catheter having a balloon is inserted through the access artery, e.g., the femoral artery in the patient's leg or the radial artery in the arm, and advanced through the vascular system to the occluded site over a wire. The deflated balloon is placed at the occlusion and the balloon is inflated to crack and stretch the plaque and other deposits to expand the opening in the vessel. Balloon angioplasty, especially in coronary surgery, is frequently immediately followed by insertion of a stent, a small metallic expandable device which is placed inside the vessel wall to retain the opening which was created by the balloon. Balloon angioplasty has several drawbacks including difficulty in forcing the balloon through the partially occluded passageway if there is hard occlusion, the risk involved in cutting off blood flow when the balloon is fully inflated, and the frequency of restenosis after a short period of time since the plaque is essentially stretched or cracked and not removed from the vessel wall or because of the development of intimal hyperplasia.

Another minimally invasive technique used to treat arteriosclerosis is referred to as atherectomy and involves removal of the plaque by a cutting or abrading instrument. This technique provides a minimally invasive alternative to bypass surgery techniques described above as well as can provide an advantage over balloon angioplasty methods in certain instances. Atherectomy procedures typically involve inserting a cutting or ablating device through the access artery, e.g., the femoral artery or the radial artery, advancing it through the vascular system to the occluded region, and rotating the device at high speed to cut through or ablate the plaque over the wire. The removed plaque or material can then be suctioned out of the vessel or be of such fine diameter that it is cleared by the reticuloendothelial system. Removal of the plaque in an atherectomy procedure has an advantage over balloon angioplasty plaque displacement since it debulks the material.

Examples of atherectomy devices in the prior art include U.S. Pat. Nos. 4,990,134, 5,681,336, 5,938,670, and 6,015,420. These devices have elliptical shaped tips which are rotated at high speeds to cut away the plaque and other deposits on the interior vessel wall. Other well-known devices are the Rotablator marketed by Boston Scientific Corp. and the Diamondback Sheath 360 and Stealth 360 marketed by CSI. Other examples of atherectomy tips are disclosed in U.S. Pat. Nos. 5,217,474 and 6,096,054 and 6,676,698

It would be advantageous to enhance removal of the small particles once dislodged by the atherectomy tip.

SUMMARY

The present invention provides in accordance with one aspect a surgical atherectomy apparatus for removing particles such as plaque from an interior of a vessel comprising an outer housing and a motor housing positioned within the outer housing and containing a motor therein. The motor housing is slidable axially between a proximal position and a distal position. An axially fixed sheath extends from the outer housing. A catheter is connected to the motor housing and has a lumen and is positioned within the sheath. A rotatable shaft is positioned within the lumen of the catheter and is operatively connected to the motor for rotational movement, the rotatable shaft and catheter axially movable by movement of the motor housing between the proximal and distal positions. The rotatable shaft has an atherectomy bit extending therefrom for dislodgement of particles when rotated by the motor, wherein particles dislodged by the atherectomy bit are aspirated in the lumen of the catheter in the space between an outer wall of the rotatable shaft and an inner wall of the catheter.

In some embodiments, the particles are aspirated by a vacuum through a tube extending from an outlet port of the catheter. In some embodiments, the rotatable shaft includes a series of screw threads positioned thereon, and particles are aspirated by rotation of the rotatable shaft. Preferably, the atherectomy bit extends a first distance from a distal end of the catheter in a proximal position and extends the same first distance from the distal end of the catheter in a distal position and preferably the distal end of the catheter extends a second distance from a distal end of the sheath in a proximal position and extends a third greater distance from the distal end of the sheath in a distal position.

In some embodiments, a distal end of the atherectomy bit is spaced proximally from a distalmost end of the rotatable shaft. In some embodiments, the atherectomy bit extends to only one side of the rotatable shaft.

In some embodiments, the outer housing has first and second rails positioned therein, and the motor housing is moved along the rails when moved between the retracted and extended positions.

In some embodiments, the catheter has first and second lumens and the rotatable shaft extends though the first lumen. In some embodiments, aspiration is through the second lumen and fluid is injected through the first lumen. In other embodiments, aspiration is through the first lumen in a space between an outer wall of the rotatable shaft and an inner wall of the catheter and fluid is injected through the second lumen.

In accordance with another aspect, the present invention provides a surgical atherectomy apparatus for removing particles such as plaque from an interior of a vessel, comprising an outer housing and a motor housing positioned within the outer housing and containing a motor therein. The motor housing is slidable axially between a proximal position and a distal position. An axially fixed sheath extends from the outer housing. A catheter is connected to the motor housing and has a first lumen and a second lumen, and is positioned within the sheath. A rotatable shaft is positioned within the catheter and is operatively connected to the motor for rotational movement, the rotatable shaft and catheter axially movable by movement of the motor housing between the proximal and distal positions. The rotatable shaft has an atherectomy bit extending therefrom for dislodgement of particles when rotated by the motor wherein particles dislodged by the atherectomy bit are aspirated through the catheter.

In some embodiments, aspiration is through the second lumen and fluid is injected through the first lumen of the catheter. In other embodiments, aspiration is through the first lumen of the catheter in a space between an outer wall of the rotatable shaft and an inner wall of the catheter and fluid is injected through the second lumen. In some embodiments, the rotatable shaft includes a series of screw threads positioned thereon, and particles are aspirated by rotation of the rotatable shaft and screw threads.

In some embodiments, the atherectomy bit extends a first distance from a distal end of the catheter in a retracted position and extends the same first distance from the distal end of the catheter in the extended position, and the distal end of the catheter extends a second distance from a distal end of the sheath in a retracted position and extends a third greater distance from the distal end of the sheath in the extended position.

In accordance with another aspect of the present invention, a method for removing particles such as plaque from an interior of a vessel is provided comprising the steps of:

providing an apparatus having an axially fixed sheath and a motor housing positioned within an outer housing and containing a motor therein;

moving the motor housing from a proximal position to a distal position to change an axial position of a catheter positioned within the sheath and an axial position of a rotatable shaft positioned within the catheter;

actuating the motor to rotate the rotatable shaft to rotate an atherectomy bit extending therefrom for dislodgement of particles; and aspirating particles dislodged by the atherectomy bit through the catheter.

In some embodiments, the step of aspirating particles aspirates particles in a space between an outer wall of the rotatable shaft and an inner wall of the catheter. In some embodiments, during the change of axial position of the catheter and rotatable shaft, a distance from the atherectomy bit to a distal edge of the catheter remains unchanged.

BRIEF DESCRIPTION OF THE DRAWINGS

Preferred embodiment(s) of the present disclosure are described herein with reference to the drawings wherein:

FIG. 3 is a top view of the atherectomy device of FIG. 1 with the atherectomy tip and catheter in a retracted position, and a portion of the housing removed to show internal components;

FIG. 4 is a top view similar to FIG. 3 illustrating the atherectomy bit and catheter in an extended position;

FIG. 5A is perspective view of an alternate embodiment of the atherectomy device of the present disclosure;

FIG. 5B is a view similar to FIG. 5A showing the atherectomy bit and catheter in an extended position;

DETAILED DESCRIPTION OF PREFERRED EMBODIMENTS

Figure 1:
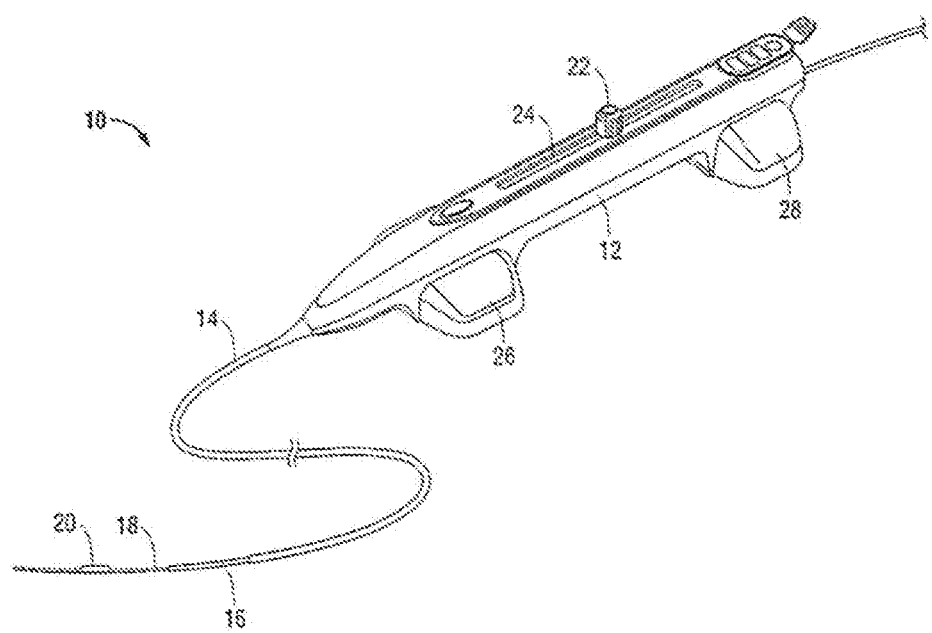
FIG. 1 is a perspective view of one embodiment of the atherectomy device of the present disclosure.

The present invention is directed to an atherectomy device (apparatus) designed for high speed rotation to remove plaque or other deposits or particles on the inside wall of the vessel to widen the blood passageway therethrough. To achieve such rotation, the rotatable atherectomy bit or tip is positioned at a distal portion of a flexible rotatable shaft that is electrically powered (or alternatively powered by gas). The shaft rotates at high speed causing the cutting or ablation surface of the bit to remove the plaque and deposits (particles) to which it comes into contact. The atherectomy bit of the present disclosure has application in a variety of vessels and structures such as for example the coronary arteries, peripheral vessels such as the tibial artery, femoral, and popliteal, and saphenous vein bypass grafts and stents.

The atherectomy bit is operatively connected to the motor housing such that activation of the motor rotates the shaft and bit. A control knob can be provided to adjust the rotational speed of the shaft and bit, and a window can be provided to visually display the speed.

In some uses, by way of example, an introducer sheath or catheter is inserted through an incision in the patient's leg, and through an incision in the femoral artery. The device is introduced through the introducer sheath into the femoral artery, and advanced to the target artery, e.g., the coronary artery, to the treatment obstruction site. Note that a guidewire in some embodiments can extend through the sheath and into the target artery so that the rotatable shaft can be inserted thereover. That is, in these embodiments, the introducer sheath is placed through a skin incision and into a vessel, e.g., the femoral artery in the patient's leg, to provide access to the target site. A guidewire is then inserted through the introducer sheath and advanced through the appropriate vessels to the target obstructed site, such as the peripheral or the coronary artery. The device is then inserted through the introducer sheath with the flexible shaft threaded over the length of the guidewire to the target obstructed site. Optionally, the guidewire can then be removed. Actuation of the motor spins the shaft and bit so the cutting surface repeatedly comes into contact with the obstruction, e.g., plaque, to remove it from the vessel wall.

The atherectomy device of the present disclosure provides for aspiration of the particles (deposits) dislodged by the high speed rotational movement of the rotatable atherectomy bit. The aspiration is through an aspiration catheter or lumen which is a fixed distance from the atherectomy bit, and the fixed distance remains constant during advancement and retraction of the atherectomy tip with respect to the device housing.

The various devices will now be described with detailed reference to the drawings wherein like reference numerals identify similar or like components throughout the several views. Note, as used herein, the term proximal refers to components or portions closer to the user and the term distal refers to components or portions further from the user.

Figure 1A:
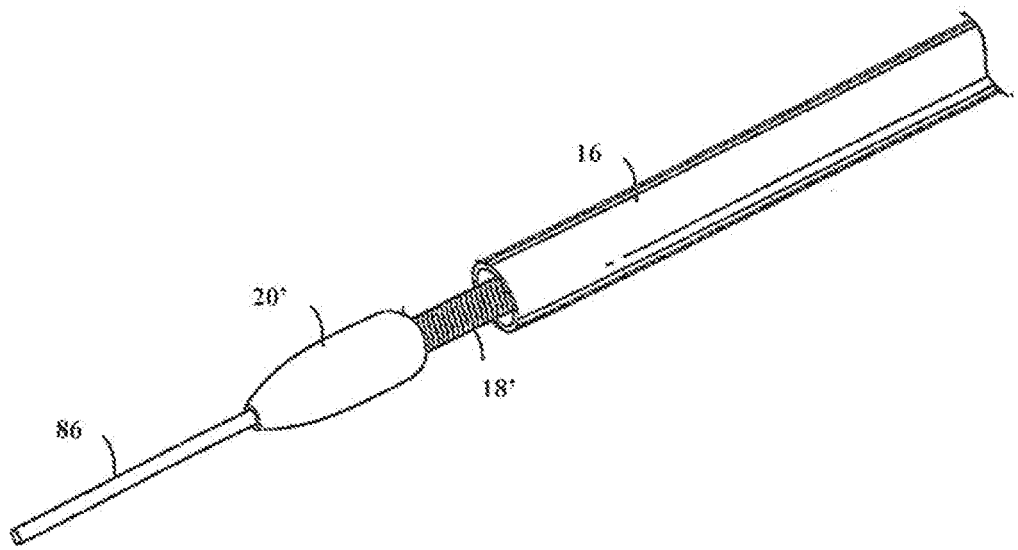
FIG. 1A is a perspective view of the atherectomy bit of an alternative embodiment of the present disclosure.
Figure 2:
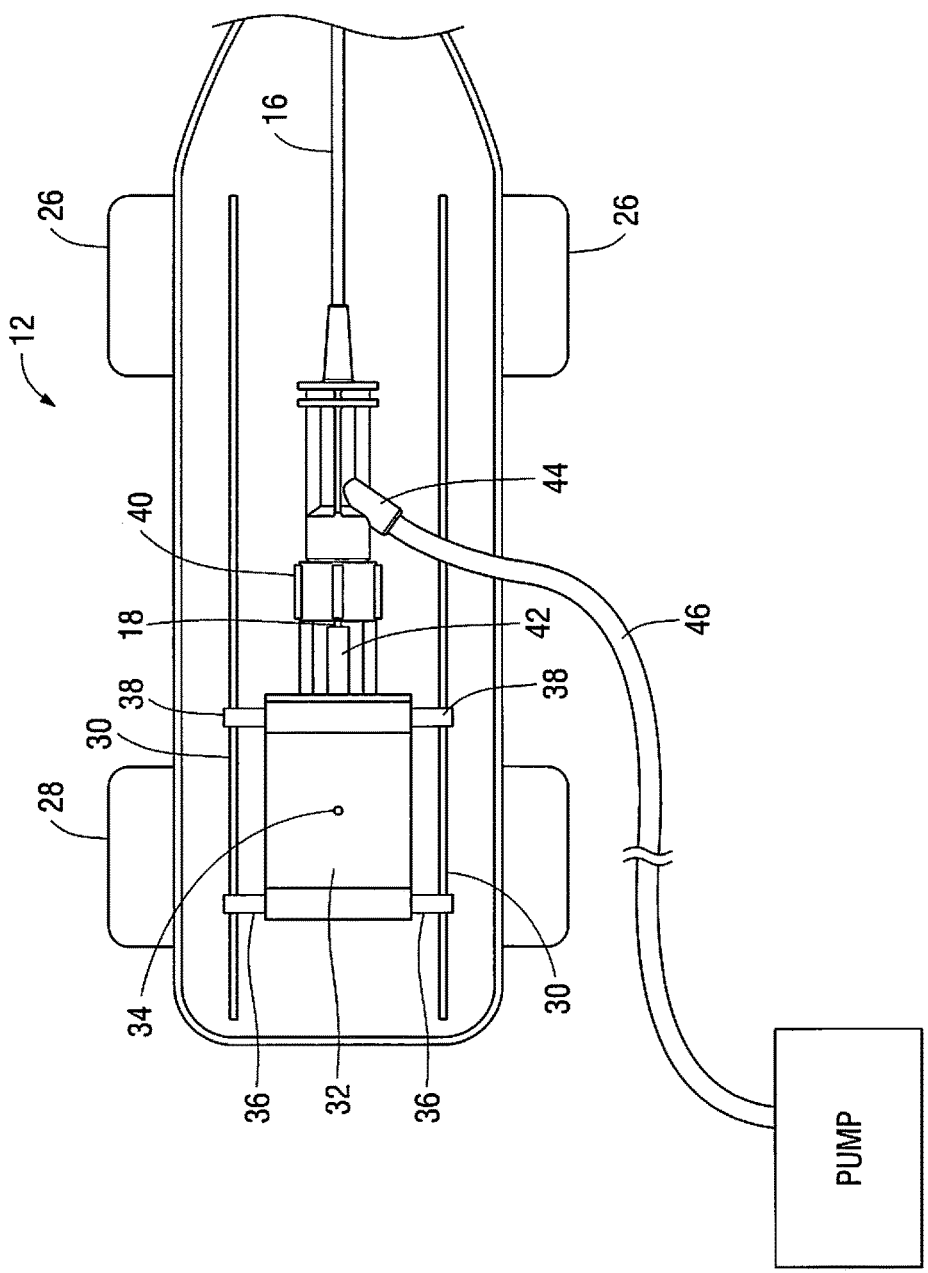
FIG. 2 is a top view of the housing portion of the device of FIG. 1, with a portion of the housing removed to show internal components.

Turning first to FIGS. 1-4, one embodiment of the atherectomy device is illustrated and designated generally by reference numeral 10. The device 10 includes an outer housing 12, an outer sheath 14 having a lumen 15 extending therethrough, a catheter 16 with a lumen 17 extending therethrough, and a rotatable shaft 18 which supports an atherectomy tip in the form of a grinding bit or burr 20. The bit 20 is preferably fixedly attached to the rotatable shaft 18 such that rotation of the shaft 18 rotates the bit 20 to dislodge the particles from the vessel wall. The bit 20 can be positioned at the distalmost end of shaft 18 or alternatively spaced proximally of the distalmost end. Also, the atherectomy bit can be eccentrically mounted on the shaft as shown in FIG. 1 or alternatively concentrically mounted and symmetrical in configuration such as shown in the alternate embodiment of FIG. 1A where elliptical bit 20' is concentrically mounted on shaft 18' which has a lumen to receive guidewire 86.

Lever 22 is positioned on the housing 12 and is configured to move the catheter 16 and shaft 18. As shown, the lever 22 is a slidable knob, slidable axially within an axial slot 24 in the housing 12. However, it should be appreciated that other actuation mechanisms are also contemplated to effect movement of the catheter 16 and shaft 18. Distal tabs 26 and proximal tabs 28, extending radially from opposing sides of housing 12, help to stabilize the housing 12 when placed on a surface outside of the patient's body.

Contained within housing 12 is a motor housing 32 which contains the motor to power the rotatable shaft 18. Motor housing 32 has a pair of proximal arms 36 and a pair of distal arms 38 extending radially from opposing sides of the motor housing 32 and engageable with the longitudinally extending rails 30 within outer housing 12. When the motor housing 32 is moved axially from a retracted position of FIG. 3 to an extended position of FIG. 4, the arms 36, 38 slide along the rails 30. Motor housing 32 includes a receiving opening 34 to receive a portion of the actuator 22, e.g., lever 22, or to receive a member which is operatively connected to the actuator 22, so that distal and proximal movement of the actuator 22 likewise moves the motor housing 32 proximally and distally along rails 30 within outer housing 12.

Hub 40 is attached to the motor housing 32, extending distally from a distal end thereof. A tube 46 can in some embodiments be provided to connect to port 44 of hub 40. Tube 46 connects to an aspiration source to aspirate particles dislodged by the atherectomy bit 20. Alternatively, tube 46 connects to a fluid pump for infusion of fluid into the lumen 17 of catheter 16. Hub 40 is attached to, or forms part of, catheter 16 which extends out the distal end 39 of housing 12. Outer sheath 14 is positioned outside the housing 12 and attached to the housing 12, extending distally from distal end 39. Outer sheath 14 can include a hub 47 having an outlet port 48 connected to an infusion source to pump fluid into the lumen 15 of sheath 14 via tubing 45, the fluid flowing between the outer wall of the catheter 16 and the inner wall of sheath 14. Alternatively, tubing 45 can connect to a suction apparatus (not shown) to aspirate particles dislodged by the atherectomy bit 20 and aspirated through lumen 15 between the outer wall of the catheter 16 and inner wall of sheath 14. Catheter 16 extends within housing 12 and through the outer sheath 14, terminating distal of the distal end 21 of the outer sheath 14. Rotational shaft 18 extends though the catheter 16 and terminates distal of the distal end 23 of the catheter 16. The atherectomy bit 20 is exposed in both the retracted and extended positions of catheter 16. This can be appreciated by comparing FIGS. 3 and 4.

As shown in the retracted position of FIG. 3, the atherectomy bit 20 extends a first distance D1 from the distal end 23 of catheter 16 and a second distance D2 from the distal end 21 of outer sheath 14. The distal end 23 of catheter 16 is a distance D3 from the distal end 21 of outer sheath 14. When the motor housing 32 is slid distally, the catheter 16, which is attached to the motor housing 32, moves distally to define a second distance D4 between the distal end 23 of catheter 16 and the distal end 21 of sheath 14. The bit 20, which is attached to the rotatable shaft 18 which is attached to the motor shaft 42 which moves with the motor housing 32, also moves distally when the motor housing 32 is moved distally to define a second distance D5 from the distal end 21 of sheath 14. Note distance D5 exceeds distance D2 and distance D4 exceeds distance D3. However, the bit 20 remains the same distance D1 from the distal end 23 of catheter 16. This is due to the rotatable shaft 18 being fixed to the motor shaft 42 which is attached to the motor which is positioned within the motor housing 32 and thus moves with the motor housing 32. Thus, when the motor housing 32 is moved a certain distance, the catheter 16 attached to the motor housing 32 moves that same distance as does the rotatable shaft 18 which is attached to the motor shaft 42. Note the sheath 14 remains axially fixed when the motor housing 32 is moved axially, with the catheter 16 and rotatable shaft 18 sliding within the lumen 15 sheath 14. When the motor housing 32 is slid proximally from the position of FIG. 4, it carries the catheter 16 and rotatable shaft 18 proximally back to the position of FIG. 3. Note FIG. 4 shows the fully extended position of the atherectomy bit 20 and catheter 16, it being understood that the bit 20 can be advanced shorter distances relative to sheath 14 and occupy a number of positions between the fully retracted position of FIG. 3 and the fully extended position of FIG. 4.

With the bit 20 in the desired retracted or extended position, the motor is actuated to rotate shaft 18 and attached bit 20 to dislodge particles. The dislodged particles are suctioned (aspirated) via vacuum through lumen 17 of catheter 16, i.e., in the space between the outer wall of rotatable shaft 18 and the inner wall of catheter 16 and out through port 44. Additional aspiration can occur, if provided, by vacuum through the lumen 15 in sheath 14, i.e., in the space between the outer wall of catheter 16 and the inner wall of sheath 14 and out through port 48 of hub 47. Also, alternatively, fluid can be infused through lumen 15. Note the bit is retracted and extended throughout the procedure while actuated. That is, it would be started in one position, e.g., the retracted position, and be turned on and pushed back and forth a couple of times during the procedure.

In use, the atherectomy device is inserted to the target site, e.g., adjacent plaque to be removed from the vessel wall. As explained above, the device 10 is inserted with a distal portion of the catheter 16, a distal region of the shaft 18 and the bit 20 exposed from the sheath 14, i.e., extending distally thereof, as shown in FIG. 3. The motor can be actuated in this position or the catheter 16 and bit 20 can be advanced distally relative to the sheath 14 a desired distance, with FIG. 4 representing the maximum distance the catheter 16 and tip 20 can extend from the sheath 14. Note the maximum distance is defined as the distal limit of advancement of the motor housing 32 within housing 12, which can be defined, for example, by the length of the rails 30. As the rotating tip 20 dislodges plaque, it can be aspirated through lumen 17 of catheter 16 and/or through lumen 15 of sheath 14 as described above.

FIGS. 5A and 5B illustrate an alternate embodiment of the atherectomy device wherein instead of providing a vacuum source for aspiration a screw thread is provided on the rotating shaft 58 to remove particles. The atherectomy device of FIGS. 5A and 5B is designated by reference numeral 50 and has a catheter 56, similar to catheter 16 of FIG. 1, a sheath 54 similar to sheath 14 of FIG. 1 and a rotatable shaft 58 with atherectomy bit or tip 60 similar to bit 20. The rotatable shaft 58 differs from shaft 18 of FIG. 1 in that it has a series of threads 62 mounted thereon. These threads 62 function as an Archimedes screw, i.e., a screw pump, to remove the particles/deposits dislodged by the tip 60. That is, as the shaft 58 is rotated, the screw's helical surface scoops the deposits and directs the deposits proximally (rearwardly) along the shaft 58 within lumen 64 of catheter 56, i.e., in the space between the outer wall of shaft 58 and the inner wall of catheter 56, to pull dislodged particles proximally. In all other respects, atherectomy device 50 is identical to atherectomy device 10, e.g., the handle with slidable motor housing to move the catheter 56 and shaft 58 in the same manner as motor housing 32 moves catheter 16 and rotatable shaft 18. As shown in FIGS. 5A and 5B, as in the embodiment of FIGS. 1-4, the distance E1 between the bit 60 and distal edge 57 of the catheter 56 remains the same in the retracted (proximal) position of FIG. 5A and the extended (distal) positions, e.g., the fully extended position of FIG. 5B, while the distance from the distal end 55 of sheath 54 changes as the catheter 56 and shaft 58 are moved distally. Infusion of fluid can be provided through lumen 66 of sheath 54, i.e., in the space between the inner wall of sheath 54 and outer wall of catheter 56. Alternatively, or in addition, aspiration can occur in lumen 64, i.e., in the space between the inner wall of catheter 56 and the outer wall of shaft 58. Note the shaft 58 has a lumen to receive guidewire 86. Shaft 18 could also be provided with a lumen to receive a guidewire.

Figure 6:
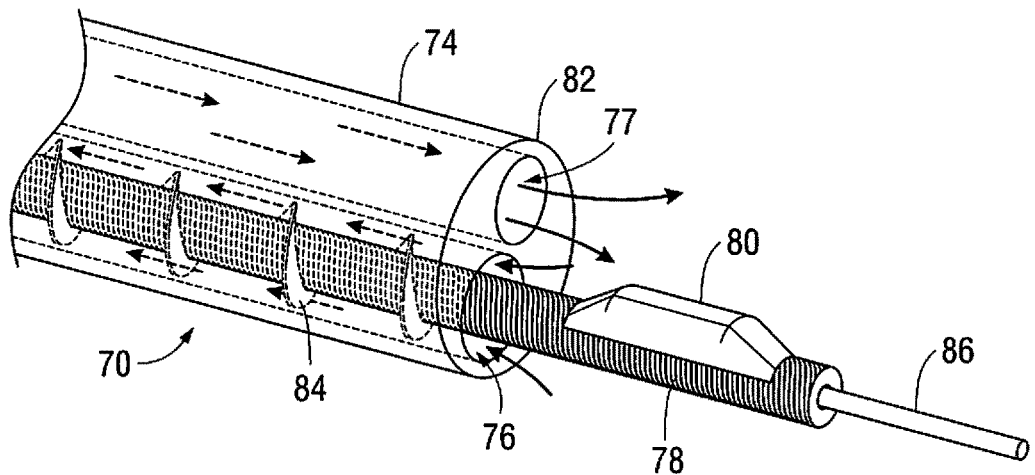
FIG. 6 is perspective view of another alternate embodiment of the atherectomy device of the present disclosure.
Figure 7:
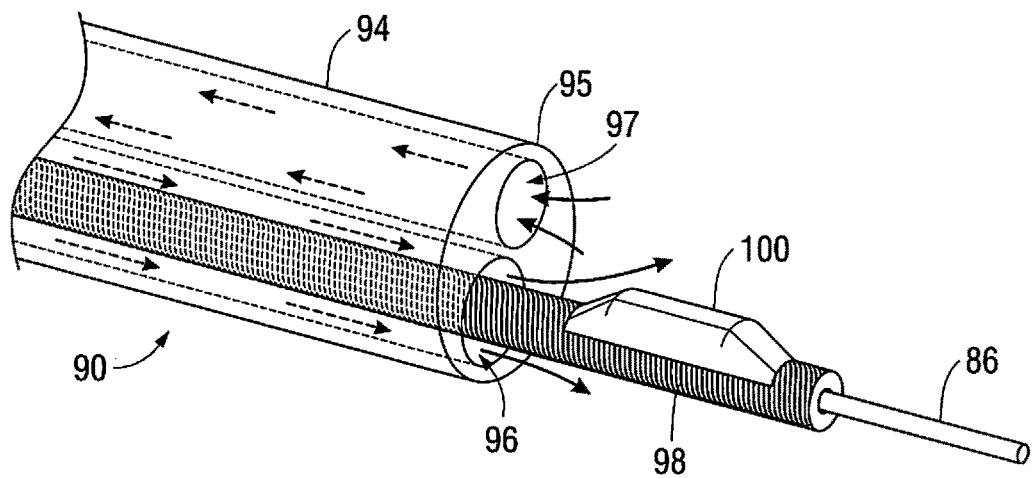
FIG. 7 is perspective view of another alternate embodiment of the atherectomy device of the present disclosure.

FIGS. 6 and 7 illustrate alternate embodiments of the atherectomy device of the present disclosure. The device 70 of FIG. 6 includes a dual lumen catheter 74. The catheter 74 is movable axially with respect to a sheath (not shown) which is identical to sheath 14 of FIG. 1. Also not shown since it is identical to the embodiment of FIG. 1 is the handle, slidable motor housing to move the catheter and shaft, etc. That is, the device 70 is identical to device 10 except for the dual lumen catheter and the screw 84 on the rotatable shaft 78. These threads 84, like threads 62 of the embodiment of FIGS. 5A-5B discussed above, function as an Archimedes screw, i.e., a screw pump, to remove the particles/deposits dislodged by the tip 80 extending from one side of rotatable shaft 78. That is, as the shaft 78 is rotated, the screw's helical surface scoops the deposits and directs the deposits proximally (rearwardly) along the shaft 78 within lumen 76 of catheter 74, i.e., in the space between the outer wall of shaft 78 and the wall of lumen 76, to pull dislodged particles proximally. As in the other embodiments disclosed herein, the shaft 78 can have a lumen to receive a guidewire 86 for over the wire insertion of the device 70. The rotatable shaft 78 extends through lumen 76 of catheter 74 with the threads 84 directing particles through lumen 76. The shaft 78 is attached to the motor and axially fixed in lumen 76 so its distance from the end of catheter 74 remains constant. That is, as in the embodiments described above, the bit 80 remains a fixed distance from the distal edge 82 of catheter 74 in proximal and distal positions of the catheter 74 as the motor housing movement moves both the catheter 74 and rotatable shaft 78 relative to the outer sheath, i.e. sheath 14, in the same manner as the embodiment of FIG. 1. Lumen 77 provides for infusion of fluids.

The atherectomy device 90 of the alternate embodiment of FIG. 7 differs from the embodiment of FIG. 6 only in that the rotatable shaft 98 does not have threads and aspiration and fluid infusion occur in different lumens of the dual lumen catheter 94 than in catheter 74. More specifically, rotatable shaft 98, which has bit 100 extending therefrom, is axially fixed in lumen 96 of catheter 94 and remains a fixed distance from distal catheter edge 95 of catheter 94 in proximal and distal positions of catheter 94, the catheter 94 moved by movement of the motor housing (not shown) in the manner described above. Fluid infusion is provided in lumen 96, i.e., in the space between the wall of lumen 96 and the outer wall of shaft 98. Note that shaft 98 includes a lumen for over the wire insertion over guidewire 86. In this embodiment of FIG. 7, aspiration of particles is through lumen 97 of catheter 94.

As noted above, the systems herein can include an aspiration source and/or fluid source. Tubing extends from the aspiration source to the catheter and from the fluid source to the catheter. An aspiration source can in addition or alternatively communicate with the introducer sheath via a port or side arm to provide aspiration in the space (gap) between the inner wall of the introducer sheath and the outer wall of the sheath. The introducer sheath can extend to a region adjacent the tip or alternatively a sleeve could be inserted through the introducer sheath and advanced over the guidewire.

In alternate embodiments of the atherectomy tip disclosed herein, longitudinal or elongated circular and oval cutting grooves could be provided to provide a roughened surface to cut or ablate the plaque as the tip is rotated. The grooves or indentations can be formed by laser cutting a series of grooves extending longitudinally within the interior of the tip stock and ground to remove portions of the outer surface to partially communicate with the grooves, thereby creating indentations forming a roughened surface for contact with the plaque. Another way contemplated to create the roughened surface is by blasting, e.g., sandblasting or grit blasting, the tip. The tip is held in a fixture and blasted at a certain pressure, thereby removing portions of the outer surface to create a roughened surface. Creation of a roughened surface by chemical etching is also contemplated or by applying an abrasive coating.

As noted above, the atherectomy bit (burr) of the embodiments described herein can be eccentrically or concentrically mounted, and can be of asymmetrical configuration or symmetrical configuration such as oval or elliptical, and can be positioned at the distalmost end of the rotatable shaft or spaced proximally of the distalmost end.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A surgical atherectomy apparatus for removing particles such as plaque from an interior of a vessel, the apparatus comprising:
    an outer housing;
    a motor housing positioned within the outer housing and containing a motor therein, the motor housing slidable axially between a proximal position and a distal position;
    an axially fixed sheath extending distally from the outer housing;
    a catheter connected to the motor housing and having a lumen extending therein, the catheter positioned within the axially fixed sheath, the catheter slidable within the lumen of the axially fixed sheath from a first retracted position to a second extended position, the lumen terminating in a distal opening aligned with a longitudinal axis of the catheter; and
    a rotatable shaft positioned within the lumen of the catheter and operatively connected to the motor for rotational movement with respect to the catheter, the rotatable shaft and catheter movable together in an axial direction by axial movement of the motor housing between the proximal and distal positions, the rotatable shaft having an atherectomy bit extending therefrom and axially fixed thereto for dislodgement of particles when the atherectomy bit is rotated by the motor about its axis, the atherectomy bit exposed from the catheter such that a proximal edge of the atherectomy bit is spaced distally of a distal edge of the catheter in both the retracted and extended positions of the catheter and positioned distal of the distal opening of the catheter in the retracted and extended positions of the catheter, wherein the motor housing moves the catheter and rotatable shaft a same distance so the atherectomy bit extends a first distance from the distal opening of the catheter in the proximal position of the motor housing and extends the same first distance from the distal opening of the catheter in the distal position of the motor housing and extends a third distance from a distal end of the axially fixed sheath in the retracted position of the catheter and extends a fourth distance from the distal end of the axially fixed sheath in the extended position of the catheter, the fourth distance being greater than the third distance, the distance of the bit from the distal opening of the catheter remaining constant during rotation of the bit to dislodge particles;
    wherein particles dislodged by the rotatable atherectomy bit are aspirated through the distal opening in the catheter and the lumen of the catheter in a space between an outer wall of the rotatable shaft and an inner wall of the catheter.

2. The surgical apparatus of claim 1, wherein the particles are aspirated by a vacuum through a tube extending from an outlet port of the catheter.

3. The surgical apparatus of claim 1, wherein the rotatable shaft includes a series of screw threads positioned thereon, and particles are aspirated by rotation of the rotatable shaft.

4. The surgical apparatus of claim 1, wherein the rotatable shaft has a threaded region to direct deposits proximally as the rotatable shaft is rotated.

5. The surgical apparatus of claim 1, wherein the outer housing has first and second rails positioned therein, and the motor housing is moved along the rails when moved between the proximal and distal positions.

6. The surgical apparatus of claim 1, wherein a distal portion of the catheter is exposed from the axially fixed sheath in the retracted and extended positions of the catheter.

\* \* \* \* \*